United States Patent [19]
Kingston et al.

[11] Patent Number: 5,319,112
[45] Date of Patent: Jun. 7, 1994

[54] METHOD FOR THE CONVERSION OF CEPHALOMANNINE TO TAXOL AND FOR THE PREPARATION OF N-ACYL ANALOGS OF TAXOL

[75] Inventors: David G. I. Kingston, Blacksburg; Anthony A. Molinero, Christiansburg, both of Va.

[73] Assignee: Virginia Tech Intellectual Properties, Inc., Blacksburg, Va.

[21] Appl. No.: 931,319

[22] Filed: Aug. 18, 1992

[51] Int. Cl.$^5$ ............................................. C07D 305/14
[52] U.S. Cl. ................................ 549/510; 549/511
[58] Field of Search ............................. 549/510, 511

[56] References Cited

U.S. PATENT DOCUMENTS

| | | | |
|---|---|---|---|
| 4,206,221 | 6/1980 | Miller et al. | 549/510 |
| 4,814,470 | 3/1989 | Colin et al. | 549/510 |
| 4,857,653 | 8/1989 | Colin et al. | 549/510 |
| 4,924,012 | 5/1990 | Colin et al. | 549/510 |
| 5,015,744 | 5/1991 | Holton | 549/510 |
| 5,059,699 | 10/1991 | Kingston et al. | 549/510 |

FOREIGN PATENT DOCUMENTS 0400971 12/1990 European Pat. Off. .

OTHER PUBLICATIONS

Kingston et al., "The Chemistry of Taxol, A Clinically Useful, Anti-Cancer Agent", J. Nat. Prod., 53, 1–12 (1990).
Deutsch et al., "Synthesis of Congeners and Prodrugs 3. Water-Soluble Prodrugs of Taxol With Potent Antitumor Activity", J. Med. Chem., 32,788–792 (1989).
Mangatal et al., "Application of the Vicinal Oxyamination Reaction with Asymmetric Induction to the Hemisynthesis of Taxol and Analogues", Tetrahedron, 45, 4177–4190 (1989).
Denis et al., "A Highly Efficient, Practical Approach to Natural Taxol", J. Am. Chem. Soc., 110, 5917–5919 (1988).
Magri et al., J. Org. Chem., 51, 30–39, (1986).
Mathew et al., "Synthesis and Evaluation of Some Water-Soluble Prodrugs and Derivatives of Taxol with Antitumor Activity", J. Med. Chem., 35, 145–151 (1992).
Swindell et al., "Biologically Active Taxol Analogs With Deleted A-Ring Side-Chain Substituents and Variable C-2' Configurations", J. Med. Chem., 34, 1176–1184 (1991).
Powell et al., "Cephalomannine; A New Antitumor Alkaloid for *Cephalotaxus mannii*", Chem. Comm., 102–104 (1979).
McGuire et al., "Taxol: A Unique Antineoplastic Agent with Significant Activity in Advanced Ovarian Epithelial Neoplasms", Ann. Int. Med., 111, 273–279 (1989).
Holmes et al., "Phase II Trial of Taxol, an Active Drug in the Treatment of Metastatic Breast Cancer", J. Nat. Can. Inst., 24, 1791–1805 (1991).
Rowinsky et al., "Taxol: Twenty Years Later, the Story Unfolds", J. Nat. Can. Inst., 24, 1778–1781 (1991).
Gueritte-Voegelein et al., "Chemical Studies of 10–Deacetyl Baccatin III. Hemisynthesis of Taxol Derivatives", Tetrahedron, 42, 4451–4460 (1986).
Kingston, "The Chemistry of Taxol", Pharmac. Ther., 52, 1–34 (1991).

(List continued on next page.)

*Primary Examiner*—C. Warren Ivy
*Assistant Examiner*—Ba K. Trinh
*Attorney, Agent, or Firm*—Mason, Fenwick & Lawrence

[57] ABSTRACT

The natural product cephalomannine can be converted to the important anticancer natural product taxol by a simple process involving the steps of hydrogenation, benzoylation at the C-2'-position, protection of the C-7 position, and reaction with oxalyl chloride, followed by reaction with diphenylcarbodiimide and deprotection. The same process can be applied to mixtures of taxol and cephalomannine, thus obviating the need for the separation of these closely related compounds. In addition, the selection of an acylating reagent other than the benzoyl group allows the preparation of taxol analogs with other N-acyl substituents.

12 Claims, 6 Drawing Sheets

OTHER PUBLICATIONS

Ringel et al., "Studies with RP 56976 (Taxotere): A Semisynthetic Analogue of Taxol", J. Nat. Can., Inst., 4, 288-291 (1991).

Gueritte-Voegelein et al., "Relationships Between the Structure of Taxol Analogues and Their Antimitotic Activity", J. Med. Chem., 34, 992-998 (1991).

Miller et al., "Antileukemic Alkaloids from Taxus Wallichiana Zucc.", J. Org. Chem., 46, 1469-1474 (1981).

Shiozaki et al., "Cleavage and Some Modifications of the 7-Amide Group of the Cephamycins", Tetrahedron, 36, 2735-2740 (1980).

Shiozaki et al., "A New Method for Cleavage 7-Amide Group of Cephalosporins", Tetrahedron Lett., 46, 4059-4062 (1977).

METHOD FOR THE CONVERSION OF CEPHALOMANNINE TO TAXOL AND FOR THE PREPARATION OF N-ACYL ANALOGS OF TAXOL

FIELD OF THE INVENTION

The present invention relates to taxol, taxol congeners, taxol analogues, and methods for making same. The invention relates more particularly to the synthesis of taxol or taxol congeners from natural products having portions of the taxol structure.

BACKGROUND OF THE INVENTION

Taxol is a naturally occurring diterpenoid which has demonstrated great potential as an anti-cancer drug. Taxol, shown below as compound 1, can be isolated from the bark of the western yew, *Taxus brevifolia*, and is also found in several other yew species such as *T. baccata* and *T. cuspidata*. For further information regarding taxol, see Kingston et al., U.S. Pat. No. 5,059,699. All patents, articles, and other documents cited herein are incorporated by reference as if reproduced in full below.

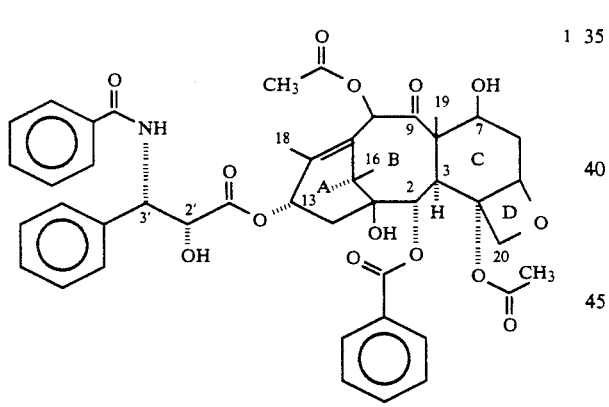

Taxol almost always co-occurs with the closely related compound cephalomannine, shown below as compound 2. Due to their close structural similarity, the separation of taxol from cephalomannine is a very difficult one. See Wani et al., "Plant Antitumor Agents. VI. The Isolation and Structure of Taxol, A Novel Antileukemic and Antitumor Agent from *Taxus brevifolia*," *J. Am. Chem. Soc.* 93, 2325(1971); Powell et al., "Cephalomannine; A New Antitumor Alkaloid from *Cephalotaxus mannii*," *J. Chem. Soc. Chem. Commun.* 102(1979); Miller et al., "Antileukemic Alkaloids from *Taxus wallichiana Zucc*," *J. Org. Chem.* 46, 1469(1981).

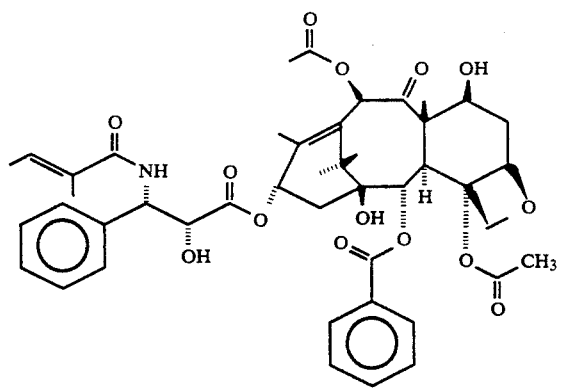

Since taxol is very scarce, a procedure to make taxol from cephalomannine would prove valuable because it would increase the supply of taxol, while also avoiding the need to separate cephalomannine from taxol.

No previous work on a direct conversion of cephalomannine to taxol has been reported. An indirect route is available through the work of Magri et al., in *Journal of Organic Chemistry*, Vol. 51, p. 3239, 1986, who reported that taxol can be converted to baccatin III, shown below as compound 3, by treatment with tetrabutylammonium borohydride in dichloromethane. It has been surprisingly discovered that this process works equally well with cephalomannine, so a pathway exists to prepare baccatin III 3 from cephalomannine.

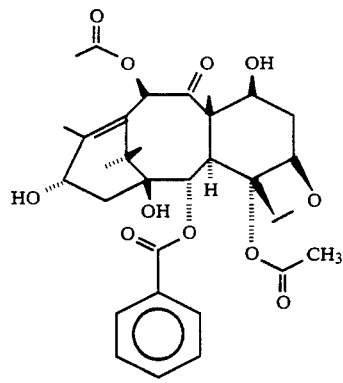

Baccatin III 3 can be converted to taxol by one of several published pathways. See Holton, R., "Method for Preparation of Taxol Using an Oxazinone," U.S. Pat. No. 5,015,744; Denis et al., "Highly Efficient Practical Approach to Natural Taxol," *J. Am. Chem. Soc.* 110, 5917(1988); Mangatal et al., "Application of the Vicinal Oxyamination Reaction with Asymmetric Induction to the Hemisynthesis of Taxol and Analogues," *Tetrahedron* 45, 4177(1989).

Hence, cephalomannine can be converted to taxol through baccatin III 3, by treatment of cephalomannine with, by way of non-limiting example, tetrabutylammonium borohydride in the presence of dichloromethane. However, this process requires the synthesis of the β-phenylisoserine side-chain of taxol in enantiomerically pure form, and the coupling of the side-chain to baccatin III 3 does not proceed quantitatively.

Because of the promising clinical activity of taxol against various types of cancer, the preparation of analogues of taxol is an important endeavor, especially in view of the previously mentioned limited supply of taxol. See McGuire et al., "Taxol: A Unique Antineoplastic Agent with Significant Activity in Advanced Ovarian Epithelial Neoplasms," *Ann. Intern. Med.* 111: 273–279 (1989); Holmes et al., "Phase II Trials of Taxol, an Active Drug in the Treatment of Metastatic Breast Cancer," *J. Natl. Cancer Inst.* 83: 1797–1805 (1991).

It is believed that the preparation of taxol analogues will result in the synthesis of compounds with comparable or greater potency than taxol (thus reducing the need for the drug), superior bioavailability, or having less undesirable side effects. Indeed, the synthesis of the taxol analogue taxotere, which differs from taxol only in the nature of the N-acyl substituent and the absence of the 10-acetyl group, indicates the usefulness of this approach, since taxotere is reported to be approximately twice as active as taxol in some assays (although taxol is believed to be more effective in other systems than taxotere). See Guéritte-Voegelein et al., "Chemical Studies of 10-Deacetylbaccatin III. Hemisynthesis of Taxol Derivatives," *Tetrahedron* 42: 4451–4460 (1986); Ringel et al., "Studies with R P56976 (Taxotere) A Semisynthetic Analogue of Taxol," *J. Natl. Cancer Inst.* 83:288–291 (1991).

A large number of taxol analogs have antitumor properties as shown by their ability to inhibit the disassembly of microtubules. See "Relationships between the Structure of Taxol Analogues and Their Antimitotic Activity," *Journal of Medicinal Chemistry,* Vol. 34, pp. 992–998 (1991); "Biologically Active Taxol Analogues with Deleted A-Ring Side Chain Substituents and Variable C-2' Configurations," *Journal of Medicinal Chemistry,* Vol. 34, pp. 1176–1184, (1991); "Synthesis and Evaluation of Some Water-Soluble Prodrugs and Derivatives of Taxol with Antitumor Activity," *Journal of Medicinal Chemistry,* Vol. 35, pp. 145–151, (1992). The foregoing articles demonstrate the effectiveness of taxol analogs as antitumor agents.

There is also a need for a method to quickly determine the biological activities of new compounds or pharmaceutical compounds having bioactivities or structures similar to taxol. The short supply and expense of taxol makes impractical the use of taxol as a standard in determining the bioactivities of other compounds; thus, it is highly desirable that a range of other standards with known biological activities be available to determine the bioactivity of taxol derivatives and other compounds relative to taxol. Useful standards should be derivatives of taxol, or the standards should be compounds which have similar structures to taxol, but which are more readily available or which can be synthesized easier than taxol. At present, some derivatives, which do not exhibit the same high biological activity as taxol, are thrown away; this waste would be eliminated by a method which uses taxol derivatives, which have significantly less biological activity than taxol, as standards in bioactivity testing, rather than utilizing more taxol, which is already in short supply and very expensive. Further, it is critical in the commercial exploitation of taxol and taxol congeners that the efficacy of taxol and taxol congeners designated for commercial sale be subjected to rigid quality standards. It is undesireable to use taxol in quality testing due to its short supply, and therefore, it is desirable to develop quality or activity screening protocols which utilize taxol analogs.

Thus, there is a need for taxol derivatives having a range of in vivo and in vitro activities, and there is a need for taxol derivatives or compounds having similar biological activities to taxol. There is a corresponding need for methods to prepare taxol derivatives and taxol congeners.

There is also a need to prepare taxol from naturally occurring mixtures, and more particularly, there is a need to convert cephalomannine, or mixtures comprising cephalomannine, to taxol.

There is also need for better methods of treating cancer, and more particularly of treating cancer with taxol analogs.

OBJECTS OF THE INVENTION

Therefore, it is a primary object of the present invention to convert cephalomannine, or a mixture comprising cephalomannine, to taxol.

It is another object of the present invention to prepare analogs of taxol.

It is a further object of this invention to develop a new method for preparing taxol and taxol congeners.

It is yet another object of the present invention to prepare intermediates that can be directly converted to taxol or taxol congeners.

It is a further object of the present invention to use taxol analogs to treat cancer.

It is a still further object of this invention to produce taxol from a naturally occurring mixture.

It is yet another object of the present invention to develop taxol analogs suitable for use in commercial quality control and screening of taxol and analogs of taxol.

SUMMARY OF THE INVENTION

These and other objects are achieved by the present invention as more fully described herein by reference to preferred non-limiting embodiments. In a first embodiment, a mixture of cephalomannine 2 and taxol 1 is converted to taxol 1 by substituting the 2-methyl-2-butenoyl moiety on the C-13 side chain of cephalomannine with a benzoyl group; more specifically, a preferred process comprises the steps of (1) hydrogenation, (2) benzoylation, (3) protection of the C-7 hydroxyl group as its trichloroethyloxycarbonyl ("troc") or other protecting group (4) reaction with oxalyl chloride followed by addition of water, (5) reaction with diphenylcarbodiimide, and (6) removal of the protective group by reduction with zinc and acetic acid (troc) or hydrolysis (TES). In a second embodiment, pure cephalomannine is converted to pure taxol by the same reaction sequence.

In a third embodiment, either taxol, taxol congeners, or cephalomannine can be converted to an N-debenzoyl-N-(alkyloxalate) analog or an N-debenzoyl-N-(N'-alkyloxamido) analog or the corresponding aryl analogs by the sequence of (1) hydrogenation (if necessary), (2) protection of the C-2' and C-7 hydroxyl groups as their 2,2,2-trichloroethyloxycarbonyl ("troc") or other protecting group derivative, and (3) reaction with oxalyl chloride followed by the addition of an appropriate alcohol or amine. The protective groups can be subsequently removed.

In a fourth embodiment, either taxol, taxol congeners or hydrogenated cephalomannine can be converted to any desired N-acyl analog by the sequence of (1) acylation with a desired acylation reagent, (2) protection of the C-7 hydroxyl group as its 2,2,2-trichloroethyloxycarbonyl ("troc") or other protecting group derivative, (3) reaction with oxalyl chloride followed by addition of water, (4) reaction with diphenylcarbodiimide, during which the acyl group at C-2' migrates to the amino group at the 3' position, and (5) removal of the protective group at C-7.

In a sixth embodiment an intermediate, useful for its ability to be directly converted to taxol or taxol congeners, can be prepared from taxol, taxol congeners or hydrogenated cephalomannine by the sequence of (1) acylation, (2) protection of the C-7 hydroxyl group as its troc or other protecting group derivative, and (3) reaction with oxalyl chloride.

In a seventh embodiment, anti-neoplastic, N-oxalyl-containing taxol derivatives are prepared.

DEFINITIONS

The terms used herein have the meanings as conventionally used in the chemical arts, unless the meaning is clearly indicated to be otherwise either by context or by specific language of the present disclosure. Definitions incorporate those used in standard texts, such as but not limited to Grant & Hackh's *Chemical Dictionary*, 5th edition, McGraw-Hill, 1987.

Taxol analogs are broadly defined herein as those analogs having the basic structure of taxol (see 1), which are substituted at the C-2, C-4, C-7, C-10, C-2', and C-3' positions by substituents which may include, but are not limited to H, hydroxy, alkoxy, amido, and ester ($RCO_2$) wherein R is hydrogen, an alkali metal, an alkyl, an alkenyl, an alkynyl, an aminio, or an aryl.

In the present invention the term iminio ion refers to the moiety:

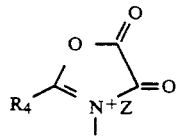

wherein Z is a counterion, preferably but not limited to $Cl^-$.

The term alkyl refers to straight-chain or branched hydrocarbons which when incorporated into taxol compounds do not substantially destroy the properties of chemical stability, water solubility and biological activity; and in some preferable embodiments alkyl refers to the lower alkyls containing from one to six carbon atoms in the principal chain and up to 10 carbon atoms; the lower alkyls may be straight or branched chain and include methyl, ethyl, propyl, isopropyl, butyl, isobutyl, tert-butyl, and the like.

The term alkyl also refers to the substituted alkyl groups which do not substantially destroy the properties of water solubility, chemical stability and biological activity including, but not limited to, the alkyl groups discussed above which have substituents such as halo, e.g., chloro, bromo; nitro; sulfate; sulfonyloxy; carboxy; carboxylate, e.g., —COO⁻; phosphate, e.g., —OP(O)(OH)₂, —OP(O)(OR)(OH), —OP(O)₂(OH)⁻, and the like; carbo-lower-alkoxy, e.g., carbomethoxy, carbethoxy; amino; mono- and di-loweralkylamino, e.g., methylamino, dimethylamino, carboxamide; sulfonamide; diethylamino, methylethylamino; amide; alkylsilyl, siloxy, lower-alkoxy, e.g., methoxy, ethoxy; lower-alkanoyloxy, e.g., acetoxy; alkenyl, alkynyl; aryl; aryloxy; and combinations of these, e.g., alkylbenzenesulfonates.

The term aryl refers to aryls with the same substituents discussed above for the substituted alkyls and also includes, but is not limited to, lower alkyl, e.g. methyl, ethyl, butyl, etc., provided the substituents do not substantially destroy the properties of chemical stability, water solubility, and biological activity.

Figure 1:
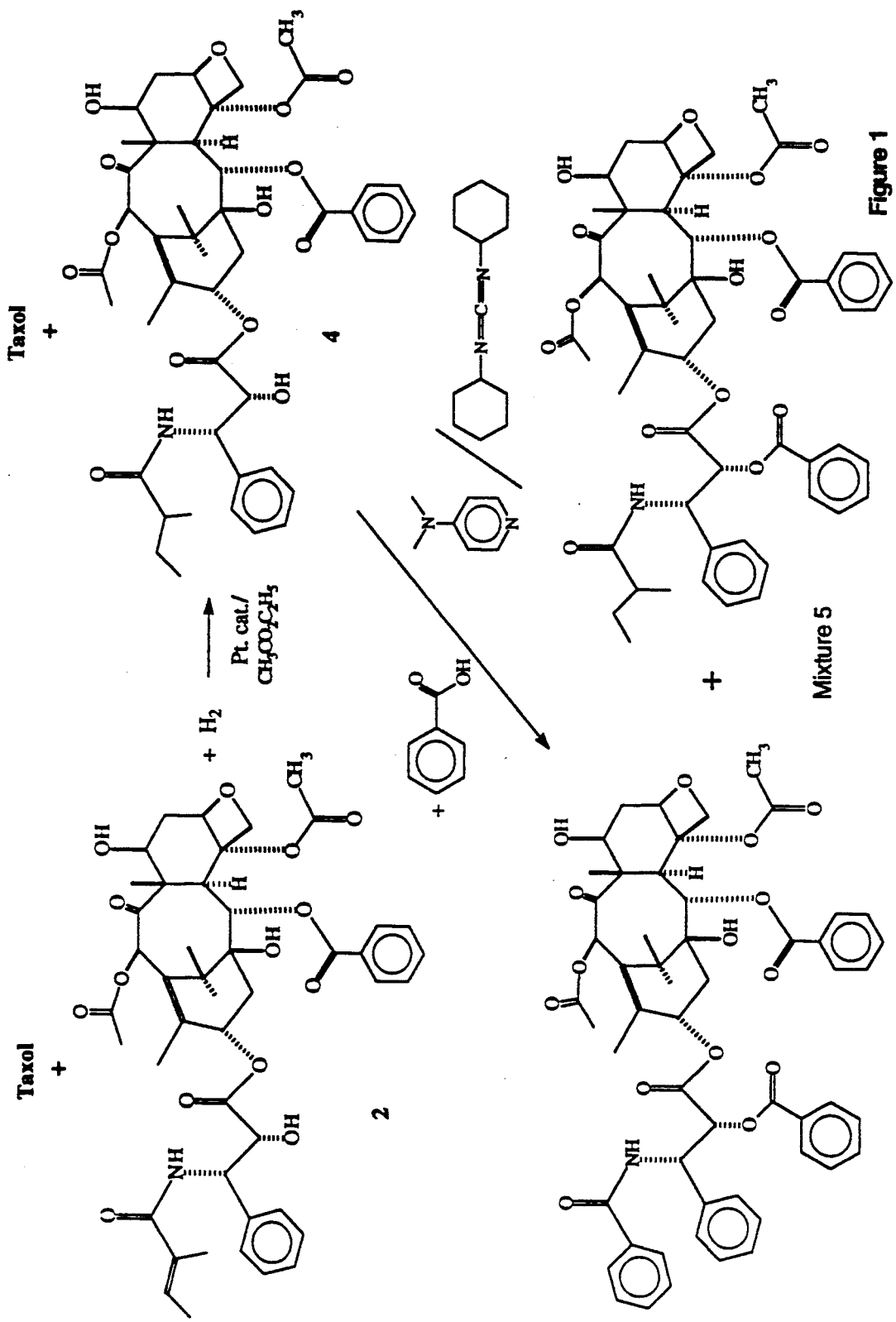
FIG. 1 illustrates steps in a preferred embodiment of the present invention involving the conversion of cephalomannine to taxol wherein a mixture of cephalomannine and taxol is hydrogenated and the hydroxyl group at the C-2' position is benzoylated.
Figure 2:
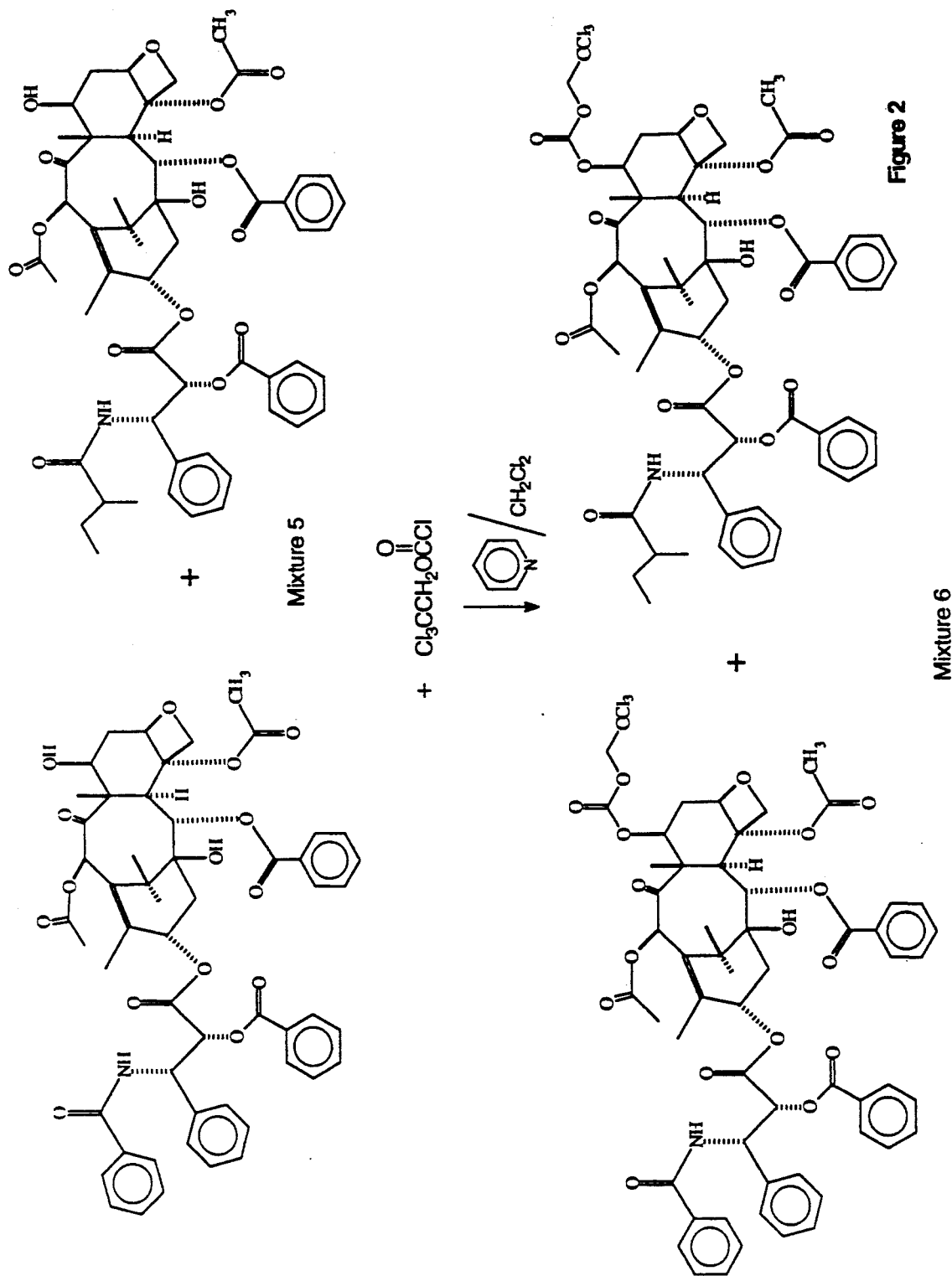
FIG. 2 illustrates a further step in the conversion of cephalomannine to taxol wherein the hydroxyl group at the C-7 position is protected by the reaction with 2,2,2-trichloroethyloxycarbonyl chloride.
Figure 3:
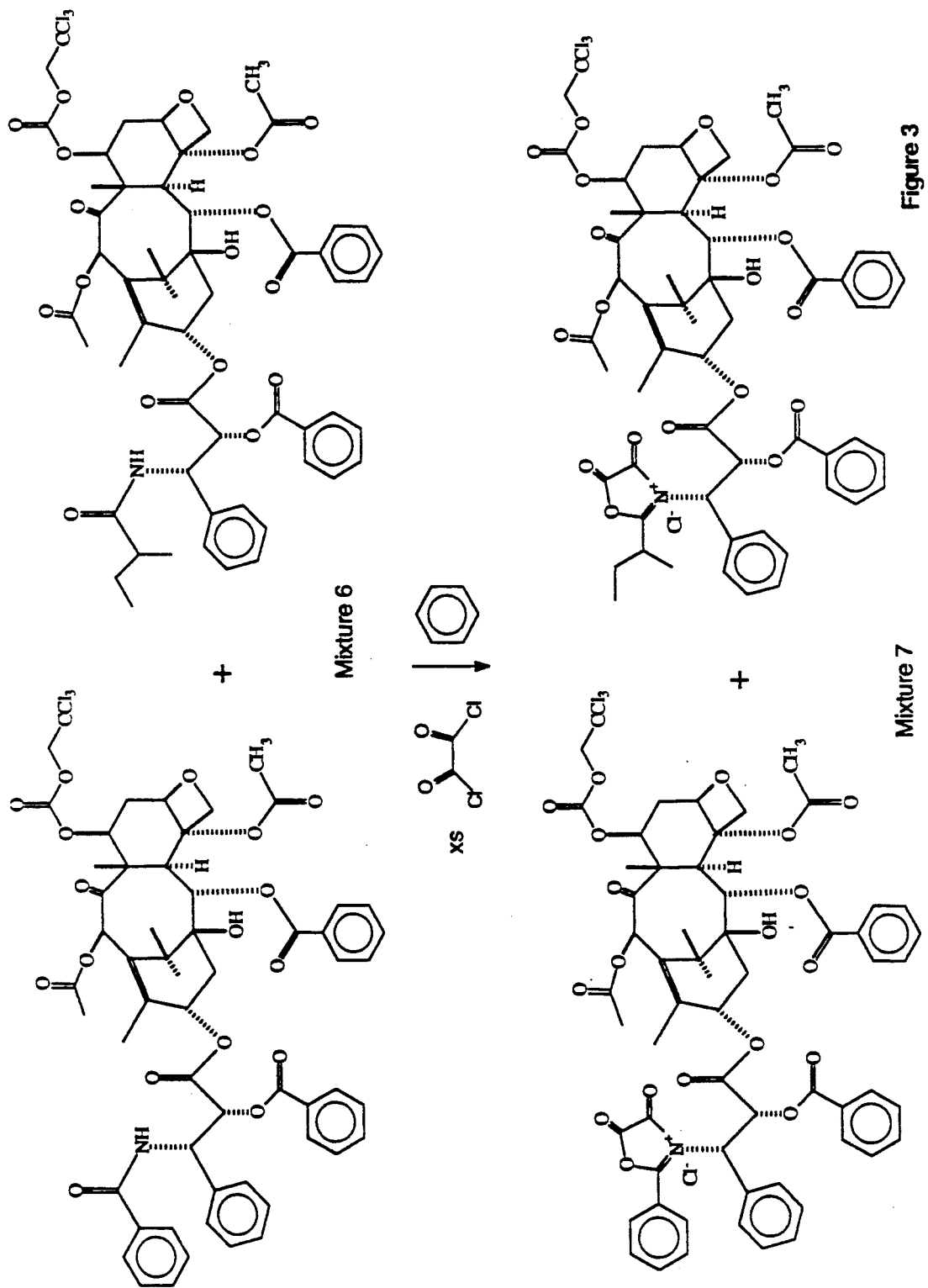
FIG. 3 illustrates a further step in the conversion of cephalomannine to taxol wherein an iminio salt is formed by the addition of oxalyl chloride.
Figure 4:
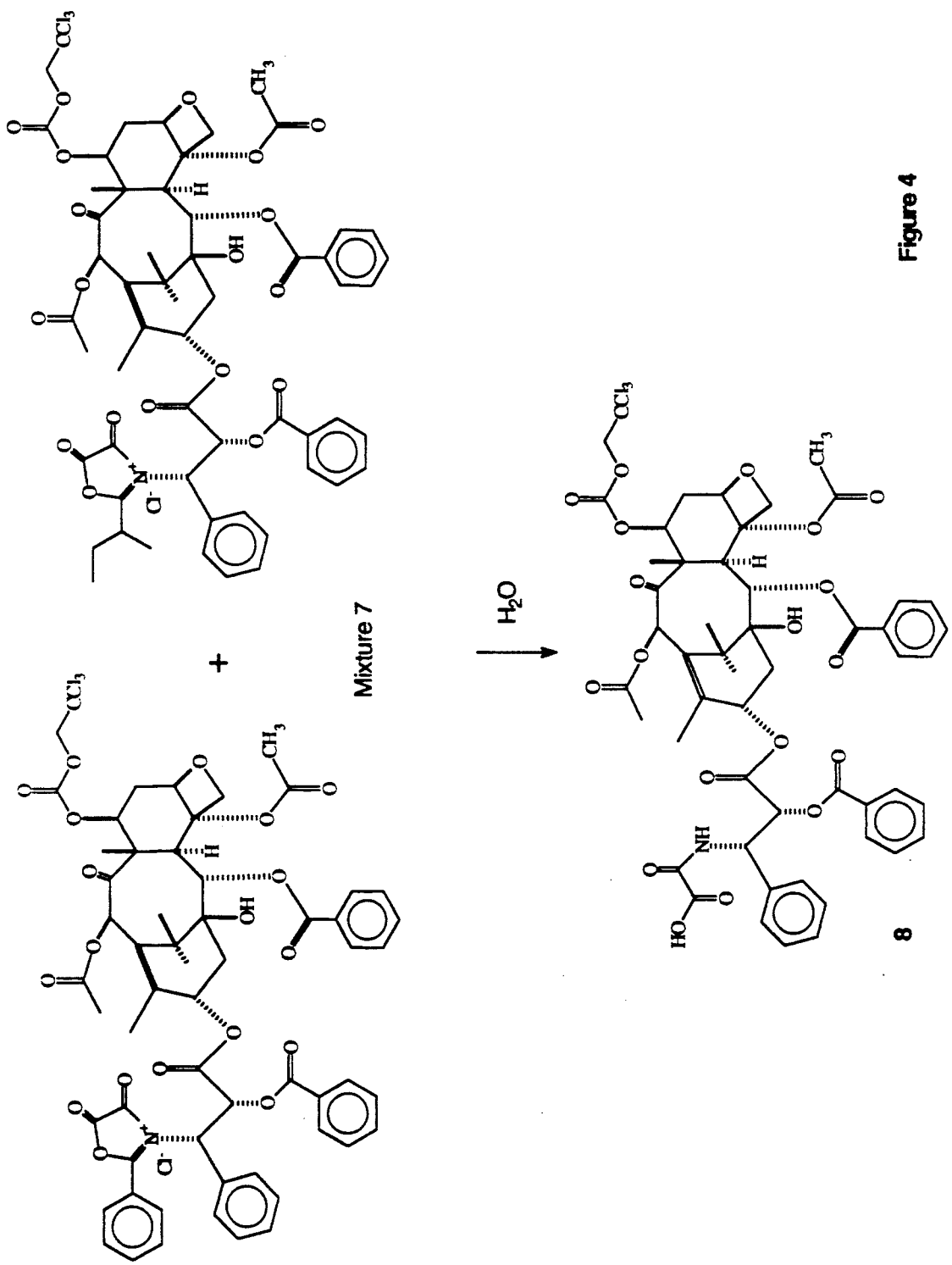
FIG. 4 illustrates a further step in the conversion of cephalomannine to taxol wherein an oxamic acid derivative is formed by the addition of water.
Figure 5:
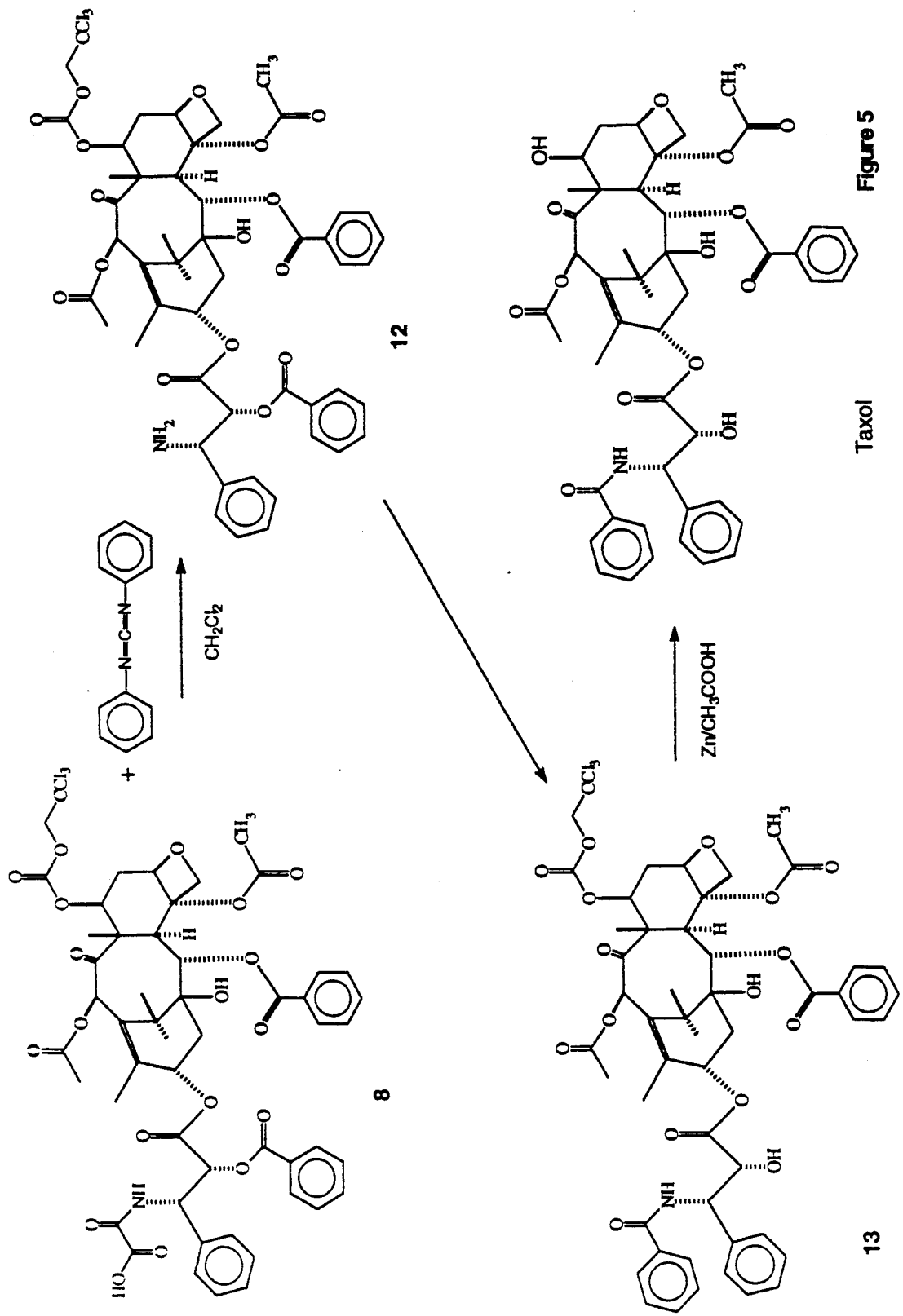
FIG. 5 illustrates a further step in the conversion of cephalomannine to taxol wherein reaction of the oxamic acid derivative with diphenylcarbodiimide, followed by removal of the protecting group by treatment with zinc and acetic acid produces taxol.
Figure 6:
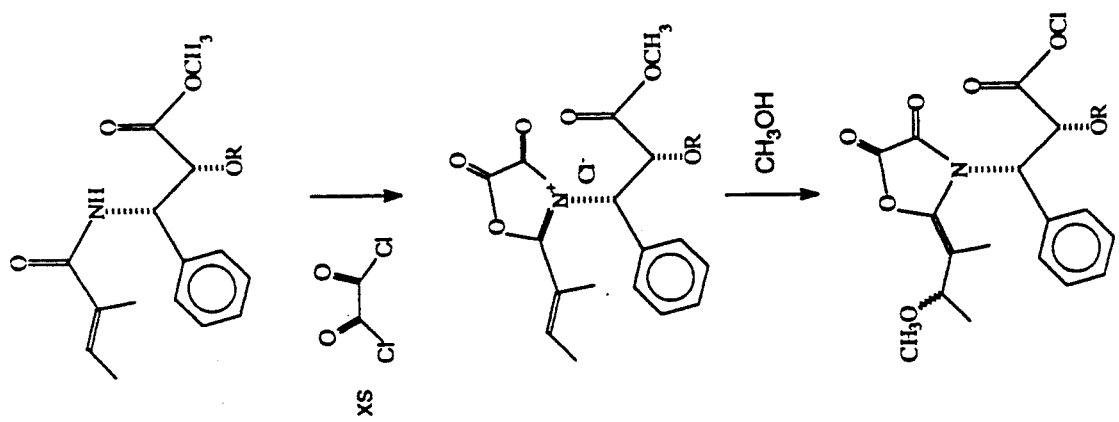
FIG. 6 illustrates a reaction using a model compound, which demonstrates the formation of a stable oxalyl heterocyclic derivative of taxol.

DETAILED DESCRIPTION OF THE INVENTION CONVERSION OF A MIXTURE OF CEPHALOMANNINE AND TAXOL TO TAXOL

With reference to FIGS. 1-5, a mixture of cephalomannine 2 and taxol 1 (about 1:1) is hydrogenated at room temperature over a platinum catalyst in ethyl acetate solution to give a mixture of taxol and dihydrocephalomannine 4 in quantitative yield. Compound 4 below

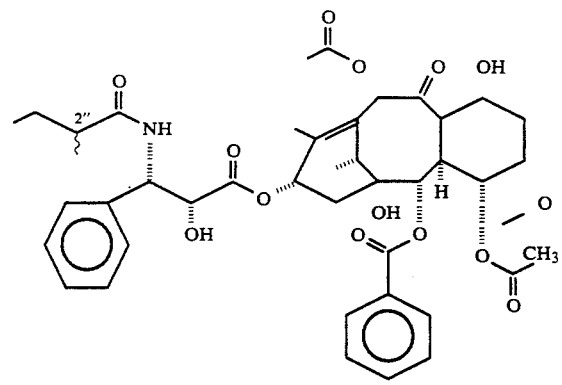

is a mixture of diastereomers at the 2''-position. The mixture was then benzoylated at the 2'-position by treatment with one equivalent of benzoic acid in the presence of an activating agent, which in a preferred embodiment comprises dicyclohexylcarbodiimide and 4-dimethylaminopyridine to yield a mixture of 2'-benzoates 5. Mixture 5, comprising the compounds 5 and 5', was then

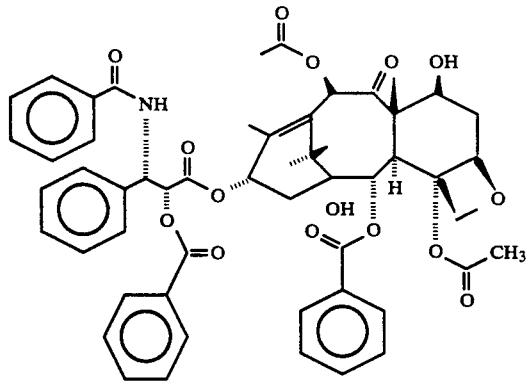

7

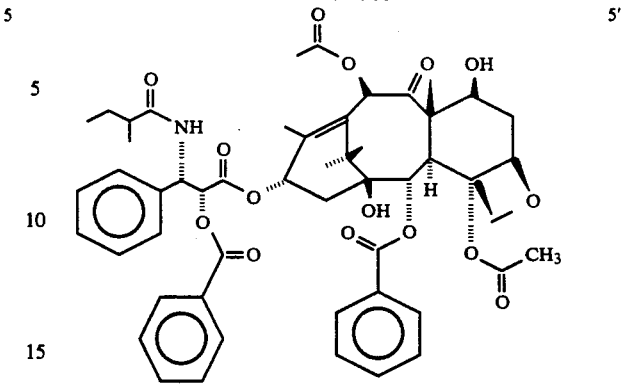

8

-continued converted to its 7-trichloroethyl oxycarbonyl derivative 6, shown below by reaction with 2,2,2-trichloroethyloxycarbonyl chloride and pyridine in methylene chloride. Purification of mixture 6 by flash chromatography gave a purified mixture in 85% yield based on the original mixture.

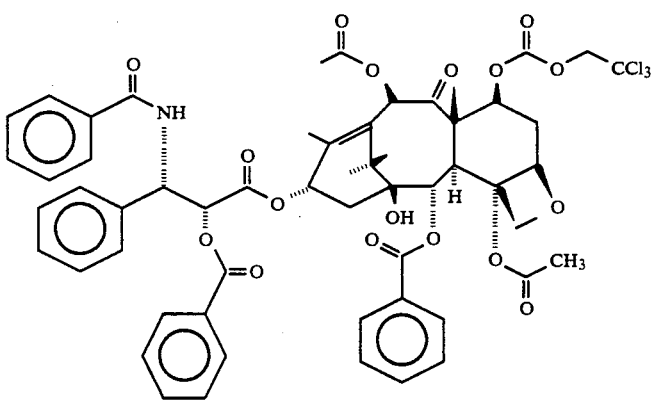

6

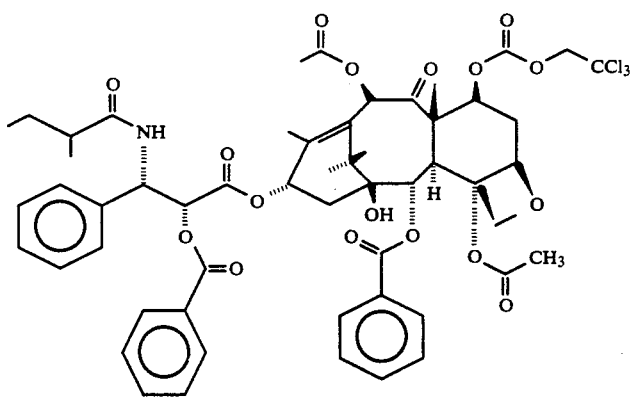

6'

Reaction of mixture 6 with excess oxalyl chloride at room temperature in benzene gave the mixture of iminio compounds 7 and 7' below.

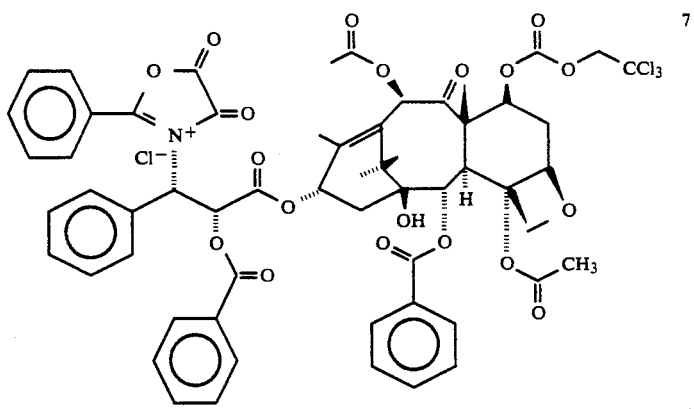

7

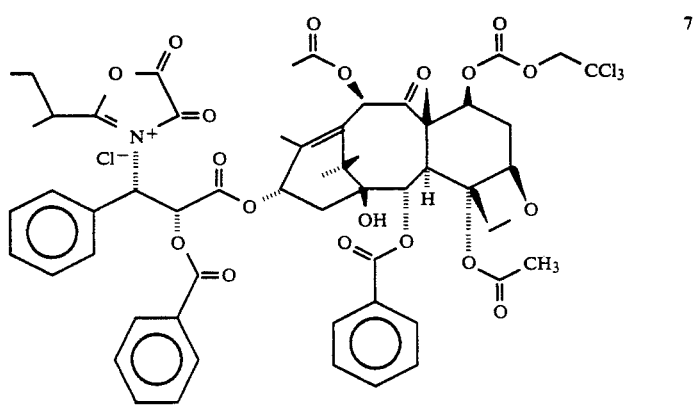

7'

Compounds 7 and 7' appeared as a white crystalline precipitate over a period of 18 hours if the reaction was cooled, but were also formed in solution over 5 hours at room temperature. More information on the reaction of amides with oxalyl chloride can be found in Chiozaki et al. "A New Method for the Cleavage of 7-Amide Group of Cephalosporins," *Tetrahedron Letters* 46, 4059 (1977). Reaction of mixture 7 with water yielded the oxamic acid derivative 8 as a single pure substance in 65% yield from mixture 6.

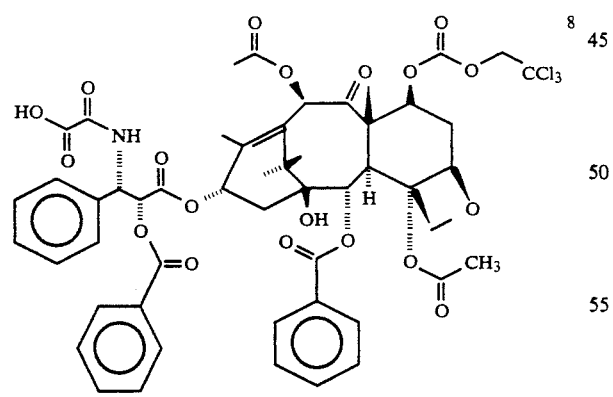

8

If the cephalomannine portion of the mixture is not hydrogenated first, reaction takes a different course. This can be illustrated by a model compound. Thus, treatment of the methyl ester 9 (R=PhCO) with oxalyl chloride yielded the iminium salt 10. Reaction of 10 with methanol, however, yielded in part the ether 11, formed by Michael addition of methanol to the αβ-unsaturated iminium salt. Similarly reaction of the non-hydrogenated cephalomannine-iminio ion with water would not form the oxamic acid derivative in good yield.

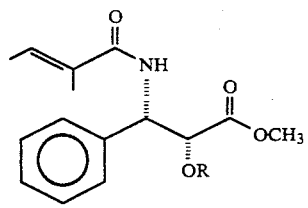

9

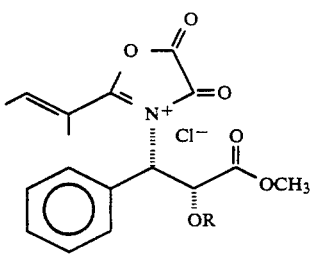

10

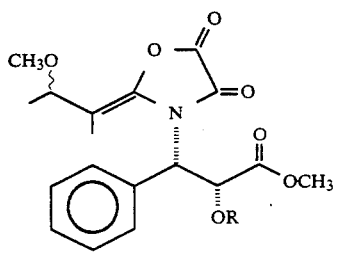

11

Conversion of oxamic acid 8 to taxol is accomplished by treatment with diphenylcarbodiimide. For more information on this type of reaction, see Shiozaki et al. in "Cleavage and Some Modifications of the 7-Amide Group of the Cephamycins," Tetrahedron 36, 2735 (1980), which discusses reaction of compounds with an oxamic acid moiety with diphenylcarbodiimide. Thus bis(2,2,2-trichloroethoxycarbonyl) derivative of the aforementioned compounds. This derivative is then converted as previously described to the 2',7-bis(2,2,2-trichloroethoxycarbonyl) analog of the iminio ion 7. Treatment of the iminio compound with methanol converted it to the N-debenzoyl-N-(methyloxalyl) taxol analog 14. The use of other alcohols, ROH, in the

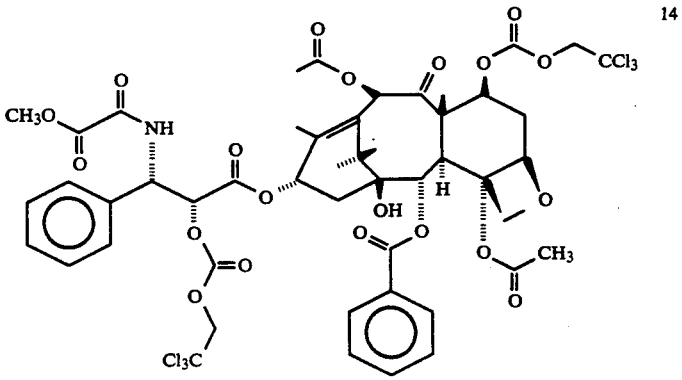

reaction of 8 with diphenylcarbodiimide in methylene chloride for 96 hours at room temperature yielded the protected taxol derivative shown below as 13. It is believed that the reaction proceeds initially to produce the amino taxol derivative shown as 12 in FIG. 5, and that O-acyl→N-acyl transfer occurs spontaneously to produce 13. Conversion of 13 to taxol 1 was achieved by treatment with zinc and acetic acid, as previously described for similar compounds.

quench process allows for the synthesis of analogs of compound 14, where the choice of alkoxy group at the 2" position of the C-13 side-chain is made by selection of the appropriate quench alcohol. The critical feature of this reaction is the presence of the nucleophilic OH group. Although, in a preferred embodiment, R is $CH_3$, the quench alcohol R-OH, may include, but is not limited to, any alkyl, arene, aryl or substituted alkyl or aryl. Illustrative, non-limiting examples of R are phenyl,

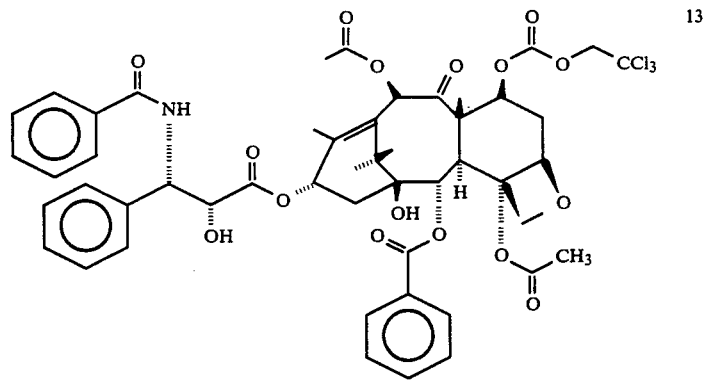

CONVERSION OF CEPHALOMANNINE TO TAXOL

Application of the reaction sequence described above to pure cephalomannine will yield pure taxol, since the reaction proceeds on a mixture of taxol and cephalomannine to yield a single pure product. In fact, experiments indicate that cephalomannine actually reacts somewhat more readily than taxol in this process.

PREPARATION OF ALKYL OXALATE ANALOGS OF TAXOL

Either pure taxol, hydrogenated cephalomannine, or a mixture comprising either or both of these compounds is protected at the 2' and 7 positions by a protecting group, and then converted as described previously to the 2',7-protected analog of the iminio ion 7. For example, use of the 2,2,2-trichloroethoxycarbonyl ("troc") protecting group results in formation of the 2',7- methylphenyl, methoxyphenyl, hydroxyphenyl, trimethoxyphenyl, chlorophenyl, nitrophenyl, aminophenyl, phenacetyl, methyl, ethyl, and t-butyl. If the quench alcohol in the above reaction is replaced by a metal hydroxide, or if the acidic proton of the oxamic acid derivative is replaced by ion exchange, then R can also be a metal such as sodium or potassium. In preferred embodiments, analogs of compound 14 are useful as anticancer agents when provided in an antineoplastically effective amount, although this may require deprotection of the C-2' and/or C-7 position to optimize such bioactivity.

An alternative preparation of analogs such as 14 is by quenching the iminio derivative with water to yield the ditroc analog 8, followed by treatment of this acid with an alcohol such as methanol and dilute mineral acid or dicyclohexylcarbodiimide (DCC). This alternate procedure is preferred for alcohols other than methanol.

The protecting group at the C-2' and C-7 positions can be removed by reaction with the appropriate reagent. For example, reaction of 14 with Zn in acetic acid converts it to the taxol analog 15.

example, reaction of 16 with zinc in acetic acid converts it to the taxol analog 17.

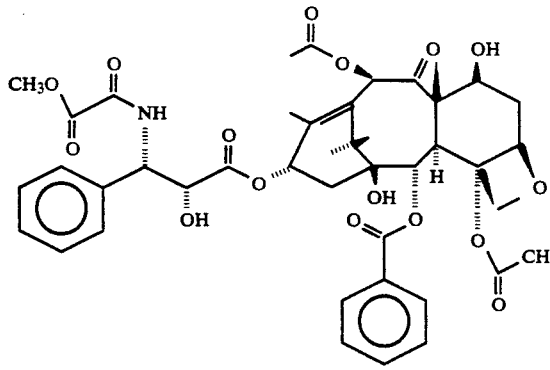

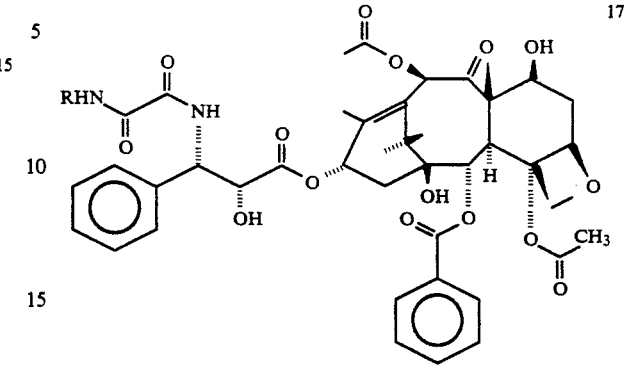

PREPARATION OF N-ALKYL OXAMIDO ANALOGS OF TAXOL

Either pure taxol, hydrogenated cephalomannine, or a mixture comprising either or both of these compounds is protected at the 2' and 7 positions by a protecting group and then converted as described previously to the 2',7-protected analog of the iminio ion 7. For example, use of the 2,2,2-trichloroethoxycarbonyl protecting group results in formation of the 2',7-bis(2,2,2-trichloroethoxycarbonyl) analog of the iminio ion 7. Treatment of this hydrogenated compound with an amine, such as by way of non-limiting example, aniline, forms the N-debenzoyl-N-(N'-phenyloxamide) analog 16 where R=Ph.

Analogs of compounds 14, 15, 16, and 17 that have an acyl group at the C-2' position are obtained by the reaction of taxol or cephalomannine or a mixture containing either or both of these compounds with an acylating reagent (e.g. benzoic acid, See FIG. 1). The resulting compound, 18, is shown below. See also, Holton, U.S. Pat. No. 5,015,744, which shows other taxol analogs, acylated at the 2' position or the 2' and 7 position, which it has been discovered are suitable for use as starting materials for producing the oxalate and oxamido derivatives of the present invention. The most reactive hydroxyl group at the 2' position will be acylated in preference to the other hydroxyl groups on the taxol or cephalomannine structure. As shown in the synthesis of 14, where the acylating reagent is 2,2,2-trichloroethyl chloroformate, conditions for acylating both positions are readily available.

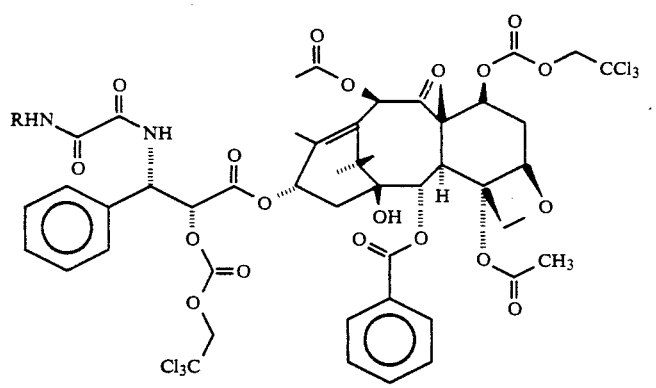

The use of other amines in the quench process allows the synthesis of any desired amide analog of compound 16, where the choice of amide, C(O)NHR, is made by the selection of the appropriate amine. Thus, R can be, but is not limited to, any alkyl, alkene, alkyne, aryl or substituted alkyl, alkene, alkyne, or aryl. Preferred analogs of compound 16 are useful as anticancer agents, when administered in an antineoplastically effective amount.

An alternate preparation of analogs such as 16 is by quenching the iminio derivative with water to yield the ditroc analog of 8, followed by treatment of this acid with an amine in the presence of DCC. This alternate procedure is preferred for amines other than aniline.

The protecting group at the 2' and 7 positions can be removed by reaction with the appropriate reagent. For Appropriate acylating reagents include, but are not limited to: carboxylic acids, carboxylic esters, anhydrides, cyclic anhydrides, amides, lactams, lactones, acid halides (also known as acyl halides), isocyanates and the substituted derivatives of these compounds. Acylation reactions sometimes require activating agents such as tertiary amines and n-butyllithium. Numerous additional acylating reagents and activating agents not specifically recited here can also be used in the present invention.

CONVERSION OF TAXOL OR CEPHALOMANNINE TO N-ACYL ANALOGS OF TAXOL

The method of the present invention as described above can be used to prepare N-acyl taxol analogs. For example, treatment of taxol with a desired acylating reagent will convert it to a 2'-acyltaxol derivative 18.

18 at the C-7 position with 2,2,2-trichloroethylchloroformate will yield the protected

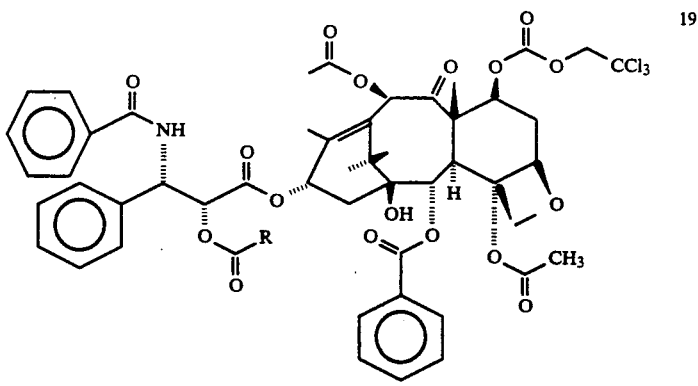

19

Protection of 18

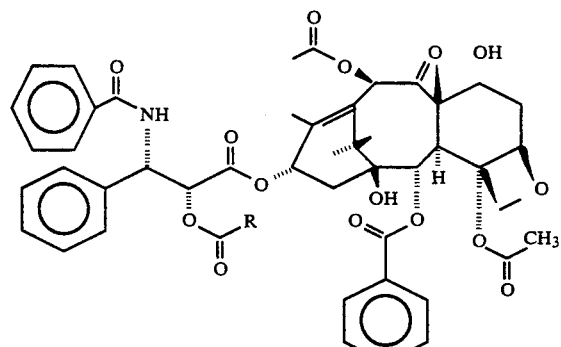

derivative 19, and treatment of 19 with oxalyl chloride followed by water as previously described will yield the oxamic acid derivative 20, where R is any desired aryl,

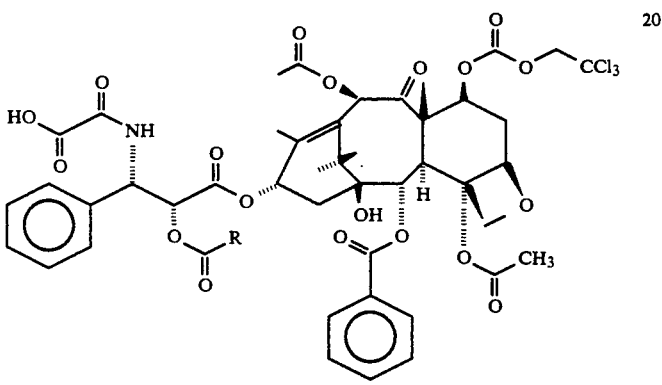

20 lower alkyl, alkenyl or alkynyl or substituted aryl or substituted alkyl group. By way of non-limiting examples, R is phenyl, hydroxyphenyl, methylphenyl, methoxyphenyl, trimethoxyphenyl, chlorophenyl, nitrophenyl, acylphenyl, phenacetyl, methyl, ethyl, and ethynyl. Treatment of 20 with diphenylcarbodiimide, as previously described, will yield the N-acyl derivative 21 by deoxyalylation

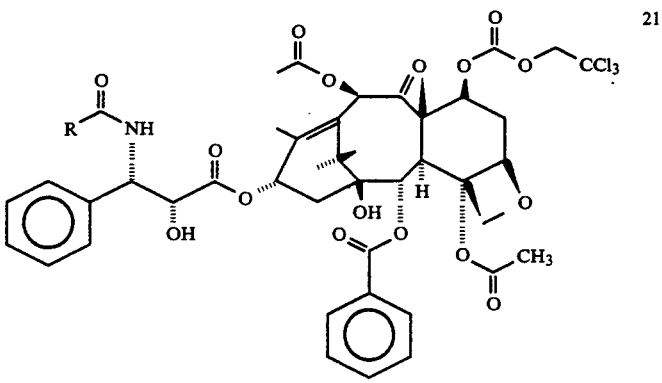

21 followed by O-acyl→N-acyl transfer. Deprotection at C-7 with zinc and acetic acid will then yield the N-acyl taxol analog 22. The same set of reactions could also be carried

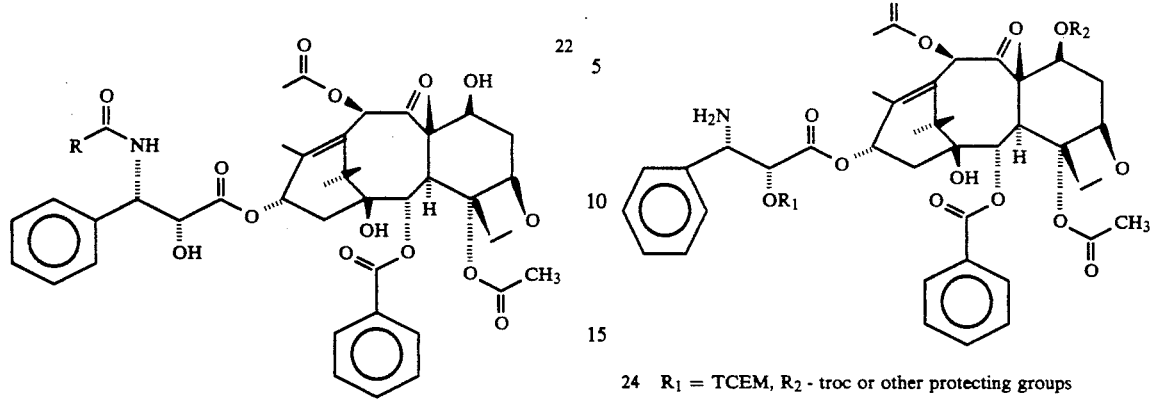

out using hydrogenated cephalomannine in place of taxol, resulting in compounds 20–22 and the 2''-isobutylated analogs of 18 and 19.

N-acyl taxol analogs are important analogs of taxol for anticancer treatment. The present invention provides a simple way of preparing such analogs from taxol or cephalomannine without removing the side-chain.

PREPARATION OF TAXOTERE FROM CEPHALOMANNINE

Hydrogenation of cephalomannine 2, to its dihydro derivative 4 can be followed by protection as the 2'-trichloroethoxy methyl ether (TCEM) -7-troc derivative 23. Other protecting groups can also be used in place of the TCEM and troc derivatives. Treatment of 23 or other 2',7 protected analogs with oxalyl chloride followed by an aqueous

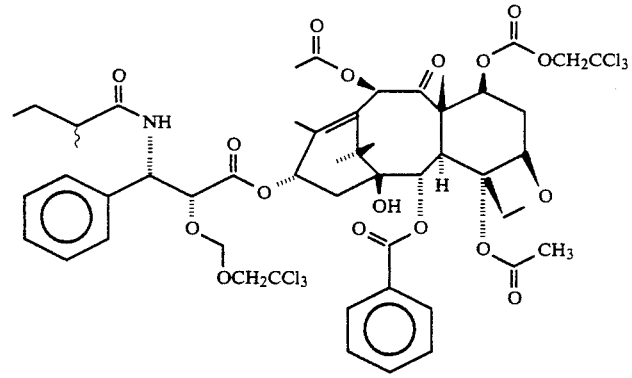

quench and subsequent reaction with diphenylcarbodiimide as previously described would give the amino derivative 24.

compound 24 can then be reacted with di-t-butyl dicarbonate to yield the 10-acetyl taxotere derivative 25. The 10-acetyl group of 25 can be hydrolyzed under mild base conditions to yield 26, and deprotection of 26 by zinc and acetic acid will yield taxotere 27. Alternatively, 25 can be deprotected first with zinc and acetic acid to yield 10-acetyl taxotere 28, and this can be hydrolyzed under very mild conditions with methanolic sodium bicarbonate to yield taxotere 27.

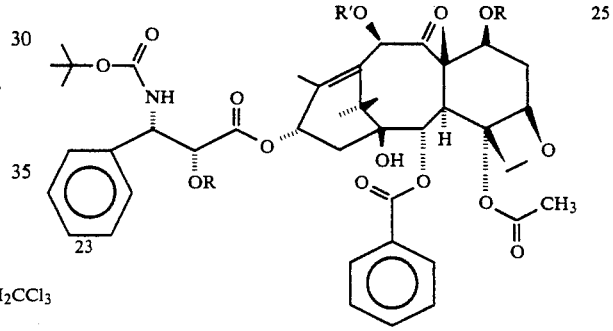

25 R = TCEM or troc or other protecting group, R' = CH$_3$CO
26 R = TCEM or troc or other protecting group, R' = H
27 R = H, R' = H
28 R = H, R' = CH$_3$CO

EXAMPLES

The following nonlimiting examples provide specific synthetic methods for the conversion of a mixture of taxol and cephalomannine into pure taxol or N-acyl analogs of taxol. Other methods and materials similar or equivalent to those described herein can be used in the practice or testing of the present invention. Proton NMR data for selected compounds is shown in Tables 1-3.

Example 1

Hydrogenation of taxol/cephalomannine

A 262 mg quantity of an approximately 50/50 mixture of taxol and cephalomannine was dissolved in 10 mL of ethyl acetate in a 100 mL round bottom flask with magnetic stirring. Then 20 mg of $PtO_2$ was added and the flask was attached to a hydrogenation apparatus. After flushing the flask five times with hydrogen gas, the solution was stirred at room temperature. After 1 hour, the flask was removed from the hydrogenation apparatus and the solution filtered through Celite to remove the catalyst. The resulting solution was evaporated to dryness under vacuum. The result was 262 mg (100%) of a mixture of taxol and dihydrocephalomannine. No further purification was performed and the sample was used as is in the next step.

2'-Benzoyl-taxol/dihydrocephalomannine

A 251 mg quantity of a taxol and dihydrocephalomannine mixture was dissolved in 10 mL of dry acetonitrile in a 50 mL round bottom flask that had been flushed with argon gas and equipped with magnetic stirring. To this solution, 41 mg of benzoic acid and 94 mg of dicyclohexylcarbodiimide were added. Finally, a few crystals of 4-dimethylaminopyridine were added. The solution was stirred at room temperature, and the reaction was monitored using TLC (Kieselgel 60 $F_{254}$, 6:4 ethyl acetate/hexane). After 5 hours the reaction was stopped by evaporating the solvent under vacuum. The crude product was purified by flash chromatography using 230-400 mesh silica gel 60 (250 mm×25 mm bed with a 9:1 chloroform/acetone eluent). The result was 268 mg (95%) of 2'-benzoyl taxol/dihydrocephalomannine.

2'-Benzoyl-7-(2,2,2-trichloroethyloxycarbonyl) taxol/dihydrocephalomannine

A 244 mg quantity of a 50/50 mixture of 2'-benzoyl taxol and 2'-benzoyl dihydrocephalomannine was dissolved in 10 mL of dry methylene chloride in a 50 mL round bottom flask that had been flushed with argon gas. Then 54 μL of 2,2,2-trichloroethylchloroformate and 32 μL of dry pyridine were added. The solution was stirred at room temperature using magnetic stirring. The reaction was monitored by TLC (Kieselgel 60 $F_{254}$, 9:1 chloroform/acetone). After 24 hours, the solution was diluted with 50 mL of ethyl acetate and washed with 2N HCl (2×50 mL), water (2×50 mL), and brine (1×50 mL). After drying with magnesium sulfate, the solvent was removed under vacuum. The crude product was purified by flash chromatography using 230-400 mesh silica gel 60 (250 mm×25 mm bed with a 9:3:1 chloroform/hexane/acetone eluent). The result was a yield of 246 mg (85%) of 2'-benzoyl-7-(2,2,2-trichloroethyloxycarbonyl) taxol/dihydrocephalomannine.

2'-Benzoyl-7-(2,2,2-trichloroethyloxycarbonyl)-N-debenzoyl-N-oxalyl taxol

A 228 mg quantity of 2'-benzoyl-7-(2,2,2-trichloroethyloxycarbonyl) taxol/dihydrocephalomannine was dissolved in HPLC grade benzene in a 25 mL round bottom flask, which had been flushed with argon gas and equipped with a magnetic stirrer. To this solution, 54 μL of oxalyl chloride was added, and the resulting solution was stirred at room temperature. After 5 hours an additional 54 μL of oxalyl chloride was added. After 12 hours, the reaction was quenched by the addition of 5 mL of acetone and 1 mL of water. The solution was stirred for 1 additional hour, and then the solvent was removed under vacuum. The crude product was purified using a preswelled Sephadex LH-20 chromatographic support (250 mm×25 mm bed). The column was eluted with 50 mL of methylene chloride followed by 100 mL of 9:1 methylene chloride/acetone. The result was a yield of 147 mg (65%) of 2'-benzoyl-7-(2,2,2-trichloroethyloxycarbonyl)-N-debenzoyl-N-oxalyl taxol.

7-(2,2,2-trichloroethyloxycarbonyl) taxol

A 13.7 mg quantity of diphenylcarbodiimide was dissolved in 2 mL of dry methylene chloride in a 15 mL round bottom flask that had been flushed with argon gas. To this solution 52 mg of 2'-benzoyl-7-(2,2,2-trichloroethyloxycarbonyl)-N-debenzoyl-N-oxalyl taxol was added. The reaction was stirred at room temperature and monitored by TLC (Kieselgel 60 $F_{254}$, 6:4 ethyl acetate/hexane). After 96 hours the reaction was stopped by removing the solvent under vacuum. The crude product was purified by preparative TLC (Analtech taperplate, 63:30:7 methylene chloride/hexane/acetone). The result was a yield of 24.5 mg (50%) of 7-(2,2,2-trichloroethyloxycarbonyl) taxol.

Taxol

A 24.5 mg quantity of 7-(2,2,2-trichloroethyloxycarbonyl) taxol was dissolved in 2 mL of acetic acid and 20 mg of zinc dust was added. The resulting heterogeneous solution was stirred at 40° C. After 2 hours, the solution was filtered to remove the zinc and diluted with 20 mL of ethyl acetate. It was then extracted with saturated sodium bicarbonate (3×20 mL) and water (2×10 mL). The organic layer was dried over magnesium sulfate and the solvent removed under vacuum. The crude product was purified by flash chromatography using 230-400 mesh silica gel 60 (320 mm×15 mm bed with a 1:1 acetone/hexane eluent). The result was 9.5 mg (47%) of taxol.

Example 2

2'7-(2,2,2-trichloroethyloxycarbonyl)-N-debenzoyl-N'-phenyloxamido taxol

A 55.5 mg quantity of 2',7-(2,2,2-trichloroethyloxycarbonyl) taxol/dihydrocephalomannine was dissolved in 2 mL of HPLC grade benzene in a round bottom flask that had been flushed with argon gas and equipped with a magnetic stirrer. To this solution 20 μL of oxalyl chloride was added and the resulting solution was stirred at room temperature. After 2 hours, an additional 20 μL of oxalyl chloride was added. When 18 hours had passed, another 10 μL of oxalyl chloride was added to drive the reaction to completion. At approximately 20 hours, 0.5 mL of the reaction mixture was quenched by the addition of 2 mL of acetone and 25 μL of aniline. Approximately 1 hour after addition of the acetone-aniline quench, the reaction was stopped by removal of the solvent under vacuum. The crude product was purified by flash chromatography using 230-400 mesh silica gel 60 (320 mm×15 mm bed with a 10:9:1 hexane/methylene chloride/acetone eluent). The result was a yield of 12.3 mg (85%) of 2',7-bis(2,2,2-trichloroethyloxycarbonyl)-N-debenzoyl-N'-phenyloxamido taxol.

TABLE 1
¹H NMR OF DERIVATIVES OF TAXOL/CEPHALOMANNINE MIXTURES

| Protons on | | Mixture of (1) and (4) | | Mixture of (6) and (6) |
|---|---|---|---|---|
| C-2 | | 5.68 (d,7) | | 5.70[b] |
| C-3 | | 3.78 (m) | | 3.95 (d,8) |
| C-5 | | 4.94 (d,10) | | 4.98 (d,11) |
| C-6 | | a | | a |
| C-7 | | 4.40 (m) | | 5.59 (m) |
| C-10 | | 6.28 (s) | | 6.38 (s) |
| C-13 | | 6.23 (t,9) | | 6.26 (s) |
| C-14 | | a | | a |
| C-16 | | 1.15 (s) | | 1.16 (s) |
| C-17 | | 1.25 (s) | | 1.21 (s) |
| C-18 | | 1.79 (s) | | 1.83 (s) |
| C-19 | | 1.66 (s) | | 1.66 (s) |
| C-20α | | 4.30 (d,6) | | 4.33 (d,8) |
| C-20β | | 4.19 (d,6) | | 4.19 (d,8) |
| C-2' | (T) | 4.79 (dd) | | 5.69[b] |
|  | (C) | 4.69 (m) | | a |
| C-3' | (T) | 5.80 (dd,7,1) | (T) | 6.05 |
|  | (C) | 5.58 (m) | (C) | 5.90 |
| 3'-NH | (T) | 7.05 (d,8) | (T) | 7.05 (d, 8) |
|  |  | a | (C) | 6.26[b] |
| 4-OAc | | 2.48 (s) | | 2.45 (s) |
| 10-OAc | | 2.24 (s) | | 2.15 (s) |
| 2-OBz,3'-NBz, 3'-Ph | | 7.35–8.15 | | 7.38–8.12 |
| 7-OCOOCH₂CCl₃ | | | | 5.02 (d,12) |
|  | | | | 4.65 (d,12) |
| 2'-OBz | | | | 7.38–8.01 |
| CH₃CH₂CH(CH₃)CO | | 0.90–2.50[c] | | 0.90–2.50[c] |

[a]Not determined due to overlapping peaks.
[b]Difficult to determine exact chemical shift due to overlapping peaks.
[c]The exact chemical shift of the protons on the hydrogenated tigloyl group is difficult to determine not only because they overlap with other peaks but also because hydrogenation of the tigloyl group creates a chiral center which leads to two diastereomers resulting in a very complex pattern.
(T) = taxol
(C) = cephalomannine

TABLE 2
¹H NMR SPECTRA OF TAXOL DERIVATIVES

| Proton on | Compound (8) | Compound (13) | Compound (17) |
|---|---|---|---|
| C-2 | 5.65[b] | 5.68 (d,7) | 5.64 (d,7) |
| C-3 | 3.95 (d,7) | 3.95 (d,7) | 3.79 (d,7) |
| C-5 | 4.95 (d,10) | 4.95 (d,10) | 4.93 (d,8) |
| C-6 | a | a | a |
| C-7 | 5.65[b] | 5.54 (m) | 4.39 (t,7) |
| C-10 | 6.35 (s) | 6.24 (s) | 6.25 (s) |
| C-13 | 6.17 (t,8) | 6.20 (t,8) | 6.25 (t,10) |
| C-14 | a | a | a |
| C-16 | 1.14 (s) | 1.17 (s) | 1.12 (s) |
| C-17 | 1.21 (s) | 1.25 (s) | 1.22 (s) |
| C-18 | 1.96 (s) | 1.85 (s) | 1.87 (s) |
| C-19 | 1.81 (s) | 1.84 (s) | 1.67 (s) |
| C-20α | 4.34 (d,8) | 4.34 (d,8) | 4.29 (d,8) |
| C-20β | 4.17 (d,8) | 4.18 (d,8) | 4.17 (d,8) |
| C-2' | 5.65[b] | 4.79 (d,3) | 4.71 (dd,5,3) |
| C-2 | 5.65[b] | 5.79 (dd,9,3) | 5.57 (dd,10,3) |
| 3'-NH | 8.15[b] | 7.05 (d,9) | 8.37 (d,10) |
| 4-OAc | 2.35 (s) | 2.39 (s) | 2.37 (s) |
| 10-OAc | 2.17 (s) | 2.17 (s) | 2.22 (s) |
| 2-OBz 3'-ph 7-OCOO | 7.35–8.20 | 7.39–8.13 | 7.28–8.10 |
| CH₂CCl₃ | 5.05 (d,12)[c] | 5.03 (d,12)[c] | |
|  | 4.67 (d,12)[c] | 4.64 (d,12)[c] | |
| 2'-OBz | 7.40–7.65[b] | | |
| 3'-NBz | | 7.39–7.77[b] | |
| oxalyl-NH | | | 8.98 (s) |

TABLE 2-continued
¹H NMR SPECTRA OF TAXOL DERIVATIVES

| Proton on | Compound (8) | Compound (13) | Compound (17) |
|---|---|---|---|
| N-Ph | | | 7.24–7.61(cm)[b] |

[a]Not determined due to overlapping peaks.
[b]Difficult to determine exact chemical shift due to overlapping peaks.
[c]The two protons on the troc group are diastereotopic.

TABLE 3
¹H NMR SPECTRA OF TAXOL

| Proton | Taxol (Prepared) | Taxol (Literature)[1] |
|---|---|---|
| C-2 | 5.67 (d,7) | 5.67 (d,7.1) |
| C-3 | 3.80 (d,7) | 3.79 (dd,7.1,1.0) |
| C-5 | 4.94 (d,8) | 4.94 (ddt,9.6,2.3,1) |
| C-6 | a | |
| C-7 | 4.40 (m) | 4.40 (ddd,10.9,6.7,4.3) |
| C-10 | 6.27 (s) | 6.27 (s) |
| C-13 | 6.23 (t,8) | 6.23 (tq,9.0,1.5) |
| C-14 | a | |
| C-16 | 1.14 (s) | 1.14 (s) |
| C-17 | 1.25 (s) | 1.24 (s) |
| C-18 | 1.79 (s) | 1.79 (d,1.5) |
| C-19 | 1.68 (s) | 1.68 (s) |
| C-20α | 4.30 (d,8) | 4.30 (ddd,8.4, 1.1, 0.8) |
| C-20β | 4.19 (d,8) | 4.19 (dd,8.5,1.0) |
| C-2' | 4.79 (br s) | 4.78 (dd,5.4,2.7) |
| C-3' | 5.79 (dd,9,3) | 5.78 (dd,8.9,2.8) |
| C'-NH | 6.99 (d,9) | 7.01 (d,8.9) |
| 4-OAc | 2.39 (s) | 2.38 (s) |
| 10-OAc | 2.24 (s) | 2.23 (s) |
| OBz,NBz,3'-Ph | 7.32–8.15 | 7.35–8.13 |

[a]Not determined due to overlappong peaks.
[1]Beutler et al. J. Nat. Prod. 55, 414 (1992).

From the above teachings it is apparent that many modifications and variations of the present invention are possible. It is therefore to be understood that the invention may be practiced otherwise than as specifically described.

We claim:

1. A method for synthesizing taxol from cephalomannine comprising the step of substituting the 2-methyl-2-butenoyl moiety on the C-13 side-chain of cephalomannine with a benzoyl group; wherein said step of substituting comprises conversion of the butenyl moiety at the C-3' position of cephalomannine to a butyl moiety via hydrogenation, and subsequent replacement of said butyl moiety with an oxalyl-containing moiety, followed by the conversion of said oxalyl-containing moiety to a benzoyl moiety.

2. A method for synthesizing taxol from cephalomannine comprising the step of attaching a benzoyl group to the C-2' position of the cephalomannine side chain, and transfer of said benzoyl group from the C-2' position onto the nitrogen at the C-3' position of the C-13 side-chain.

3. The method of claim 1, wherein said cephalomannine is present in a mixture with taxol.

4. The method of claim 1 further comprising conversion of the hydroxyl group at the C-2' position to a benzoyl group; and protection of the C-7 position with a protecting group; wherein said conversion of the hydroxyl group at the C-2' position occurs after said hydrogenation and before said replacement of said butyl moiety with an oxalyl-containing moiety, and further wherein said conversion of the hydroxyl group at the C-2' position is followed by protection of the C-7 position.

5. The method of claim 4, wherein said protecting group is selected from the group comprised of 2,2,2-trichloroethyloxycarbonyl, and trialkylsiloxy.

6. The method of claim 4, wherein said replacement of said butyl moiety with an oxalyl-containing moiety comprises formation of an iminio compound.

7. The method of claim 6, further comprising reaction of said iminio compound with water to form an oxamic acid substituent at the C-3' position of the side chain.

8. The method of claim 7, further comprising cleavage of the C-3' amido bond of said oxamic acid derivative to enable acyl transfer from the 2' position onto said N-3' position.

9. The method of claim 8, further comprising deprotection of the C-7 position to form taxol.

10. A method for converting cephalomannine to taxol comprising the following steps:
  A) hydrogenation of a first mixture comprising cephalomannine to form a second mixture comprising dihydrocephalomannine;
  B) reaction of said second mixture with benzoic acid in the presence of an activating agent to form a third mixture;
  C) reaction of said third mixture with a protecting group to form a fourth mixture comprising a derivative of said dihydrocephalomannine having a protecting group at the C-7 position;
  D) reaction of said fourth mixture with a compound capable of reacting with the side chain amino group of said dihydrocephalomannine as modified by said steps B and C to form an iminio compound;
  E) reaction of said iminio compound with water;
  F) reaction of the product of Step E with diphenylcarbodiimide to form taxol with a protecting group at the C-7 position; and
  G) removal of said protecting group at the C-7 position to form taxol.

11. The method of claim 10, wherein said iminio compound formed in Step D is formed by reaction of oxalylchloride with said dihydrocephalomannine having a protecting group at C-7.

12. A method for converting the cephalomannine in a cephalomannine-taxol mixture to taxol, comprising the steps of:
  1) hydrogenation of said cephalomannine-taxol mixture reducing the butenoyl moiety in said cephalomannine,
  2) benzoylation of the reduced cephalomannine at the C-2' position,
  3) protection of the C-7 hydroxyl group of the modified cephalomannine with a protecting group,
  4) reaction of a mixture comprising material resulting from step 3 with oxalyl chloride followed by addition of water,
  5) reaction of a solution comprising material resulting from step 4 with diphenylcarbodiimide, and
  6) removal of said protecting group from the C-7 position.

* * * * *